(12) United States Patent
Friedman

(10) Patent No.: US 9,919,106 B2
(45) Date of Patent: *Mar. 20, 2018

(54) INJECTOR DEVICE

(71) Applicant: Triangle E Medical Technologies, Inc., Concord, CA (US)

(72) Inventor: Steven A. Friedman, San Francisco, CA (US)

(73) Assignee: Steven Friedman, Concord, CA (US)

( * ) Notice: Subject to any disclaimer, the term of this patent is extended or adjusted under 35 U.S.C. 154(b) by 130 days.

This patent is subject to a terminal disclaimer.

(21) Appl. No.: 14/812,928

(22) Filed: Jul. 29, 2015

(65) Prior Publication Data

US 2015/0328411 A1  Nov. 19, 2015

Related U.S. Application Data

(63) Continuation of application No. 14/136,432, filed on Dec. 20, 2013, now Pat. No. 9,138,539, which is a
(Continued)

(51) Int. Cl.
*A61M 31/00* (2006.01)
*A61M 37/00* (2006.01)
(Continued)

(52) U.S. Cl.
CPC .............. *A61M 5/31* (2013.01); *A61M 5/008* (2013.01); *A61M 5/20* (2013.01); *A61M 5/2033* (2013.01); *A61M 5/3129* (2013.01); *A61M 5/3204* (2013.01); *A61M 5/3287* (2013.01); *G06F 19/3468* (2013.01); *H04M 1/026* (2013.01); *H04M 1/0252* (2013.01); *H04M 1/21* (2013.01); *A61M 5/28* (2013.01); *A61M 2005/206* (2013.01); *A61M 2005/2013* (2013.01); *A61M 2005/2073* (2013.01); *A61M 2005/314* (2013.01); *A61M 2205/18* (2013.01); *A61M 2205/3553* (2013.01); *A61M 2205/3569* (2013.01); *A61M 2205/3576* (2013.01); *A61M 2205/50* (2013.01); *A61M 2205/502* (2013.01); *A61M 2205/52* (2013.01);
(Continued)

(58) Field of Classification Search
CPC ........ A61M 2005/2013; A61M 5/2033; A61M 5/28; H04M 1/026; H04M 1/21; G06F 19/3468
See application file for complete search history.

(56) References Cited

U.S. PATENT DOCUMENTS 7,390,319 B2  6/2008  Friedman
7,894,095 B2  2/2011  Silverbrook et al.
(Continued)

OTHER PUBLICATIONS

AgaMatrix, Inc., iBG-Star Blood Glucose Monitoring System Owner's Guide, 88 pages, 2011, Salem, NH 03079, US.
(Continued)

*Primary Examiner* — Rebecca E Eisenberg

(57) ABSTRACT

An injector device for the percutaneous injection of fluids, such as medications, is disclosed. The device can have a mobile phone case. The mobile phone case can hold an auto-injector cartridge having a trigger, spring-loaded needle and reservoir holding a medication such as epinephrine or insulin. The device mobile phone case can communicate injection data to the phone. The phone can communicate the injection data to an emergency service provider.

12 Claims, 17 Drawing Sheets

Related U.S. Application Data continuation of application No. 13/401,015, filed on Feb. 21, 2012, now Pat. No. 8,639,288.

(60) Provisional application No. 61/463,661, filed on Feb. 22, 2011.

(51) Int. Cl.
| | |
|---|---|
| *H04M 1/00* | (2006.01) |
| *A61M 5/31* | (2006.01) |
| *A61M 5/32* | (2006.01) |
| *H04M 1/02* | (2006.01) |
| *H04M 1/21* | (2006.01) |
| *A61M 5/20* | (2006.01) |
| *G06F 19/00* | (2018.01) |
| *A61M 5/00* | (2006.01) |
| *A61M 5/28* | (2006.01) |

(52) U.S. Cl.
CPC . *A61M 2205/60* (2013.01); *A61M 2205/6054* (2013.01); *A61M 2205/6072* (2013.01)

(56) References Cited

U.S. PATENT DOCUMENTS

| | | |
|---|---|---|
| 7,914,460 B2 | 3/2011 | Melker et al. |
| 2005/0032482 A1 | 2/2005 | Brudos |
| 2006/0126304 A1 | 6/2006 | Smalc et al. |
| 2007/0181425 A1 | 8/2007 | Kim |
| 2008/0020794 A1 | 1/2008 | Garon et al. |
| 2008/0045278 A1 | 2/2008 | Kim |
| 2008/0166791 A1 | 7/2008 | Kim et al. |
| 2008/0171575 A1 | 7/2008 | Choi et al. |

OTHER PUBLICATIONS

AgaMatrix, Inc., iBG-Star Diabetes Manager App, 49 pages, 2011, Salem, NH 03079, US.

INJECTOR DEVICE

CROSS-REFERENCE TO RELATED APPLICATIONS

This application is a continuation of U.S. patent application Ser. No. 14/136,432 filed Dec. 20, 2013, which is a continuation of U.S. patent application Ser. No. 13/401,015 filed Feb. 21, 2012 (now U.S. Pat. No. 8,639,288 issued Jan. 28, 2014), which claims the benefit of U.S. Provisional Application No. 61/463,661 filed Feb. 22, 2011, the contents of each of which is incorporated by reference herein in their entireties.

BACKGROUND OF THE INVENTION

1. Field of the Invention

Devices and methods for injecting medication are disclosed. More particularly, an electronics case with integrated components for auto-injector featuring spring activation and concealed needle 2 is disclosed.

2. Description of the Related Art

Portable injectors are commonly used. Injectors such as epinephrine pens are carried by many people at risk for anaphylactic allergic reactions. If the user experiences the onset of anaphylaxis, they or a third party, can press the injector into an appropriate part of their body, such as an upper arm, thigh, abdomen, or buttocks. The injector then inserts a needle 2, usually due to the force of impact onto the body, and delivers the epinephrine to the user to treat the anaphylaxis. Often, it is useful for the user to seek follow-up treatment.

It can be difficult for one to mentally force himself or herself to self-inject. Accordingly, injectors often have a stiff, resistive cover over the needle 2 so the injector needs to be pressed into the body with a high enough force to expose the needle 2, that the injection happens extremely fast and easier to perform because the force needed to expose the needle 2 will also insert it to its full depth in the tissue instantly. However, if the user is suffered anaphylaxis, it may be difficult to muster the requisite dexterity and strength to inject oneself with a typical manual, portable pen injector.

Further, the dosage in the injector is fixed, but the needed medication for the patient may be more than available. Accordingly, if follow-up treatment is not received in a timely fashion, anaphylaxis can continue resulting in further health complications.

Portable injectors are also easily forgotten since they are often used infrequently. Users may not have them available when in need.

Accordingly, a portable injector with an auto-injection function is desired. Further, a portable injector that can summon follow-up treatment, such as emergency medical personnel is desired. A portable injector that can also be easily remembered and carried with the user is also desired.

SUMMARY OF THE INVENTION

An injector device is disclosed. The device can have a phone case and a needle 2. The phone case can have a reservoir. The needle 2 can be in fluid communication with the reservoir. The needle 2 can be spring-loaded in the case. The device can have a mobile phone 4. The phone case can be attached to the mobile phone 4, for example the phone 4 can be in the phone case. The device can have a heat shield between the mobile phone 4 and the reservoir. The reservoir can have a fluid. The fluid can include epinephrine and/or insulin.

An injector device is further disclosed that can have a frame 6 and a mobile phone 4. The frame 6 can have a reservoir, a fluid in the reservoir, an injector electric circuit, and a plug and/or outlet. The fluid can include insulin and/or epinephrine. The injector electric circuit can be in data communication with the plug or outlet. The mobile phone 4 can be in data communication with the injector electric circuit. The mobile phone 4 can be attached to the plug or outlet.

The device can have a switch, a switch cover, a trigger 8, a spring mechanically attached to the needle 2, a safety catch mechanically attached to the trigger 8 and the spring, and a needle 2 in fluid communication with the reservoir. The device can have a needle 2 channel in the trigger 8. The needle 2 can be configured to slide through the needle channel. The phone case can have a top element such as a frame top 10, a bottom element such as a frame bottom 12, and a fluid-containing element such as a cartridge 14. The top element can be separably attached to the bottom element.

A method of injecting matter into a biological body is disclosed. The method can include attaching an injector device to a mobile phone 4. The injector device can have a structural body. The injector device can have a trigger 8, a switch, a switch cover, deliverable matter such as a fluid medication, and a needle 2.

The method can include deploying the trigger 8. Deploying the trigger 8 can include activating the switch. Activating the switch can include exposing the switch. Exposing the switch can include removing the switch cover from obscuring the switch.

The method can include inserting the needle 2 through the skin. Inserting the needle 2 can include pressing the trigger 8 against the skin. The needle 2 can be spring-loaded before the inserting into the skin. The needle 2 can be held by a releasable safety catch when the needle 2 is in a retracted configuration, not yet inserted into the skin. Pressing the trigger 8 against the skin can include releasing the safety catch. The method can include delivering the deliverable matter through the needle 2 under the skin.

The method can include storing the deliverable matter in a reservoir in the structural body. The method can include thermally insulating the matter from the mobile phone 4. Thermally insulating can include attaching a removable heat shield to the structural body.

Attaching the injector device to the mobile phone 4 can include sliding a first portion of the injector device over the mobile phone 4, sliding the second portion of the injector device over the mobile phone 4, and attaching the first portion of the injector device to the second portion of the injector device. Attaching the injector device to the mobile phone 4 can include stretching the rim 16 around the phone 4.

The method can include placing the injector device in data communication with the mobile phone 4. The method can include transmitting data from the injector device to the mobile phone 4. The method can include wirelessly transmitting information over a network. The transmission of data can be caused by the pressing the trigger 8 against the skin. The transmission of data can be caused by releasing of the safety catch.

An injector assembly 17 is disclosed that can have a phone 4 and a needle 2 attached to the phone 4.

DETAILED DESCRIPTION

Figure 1:
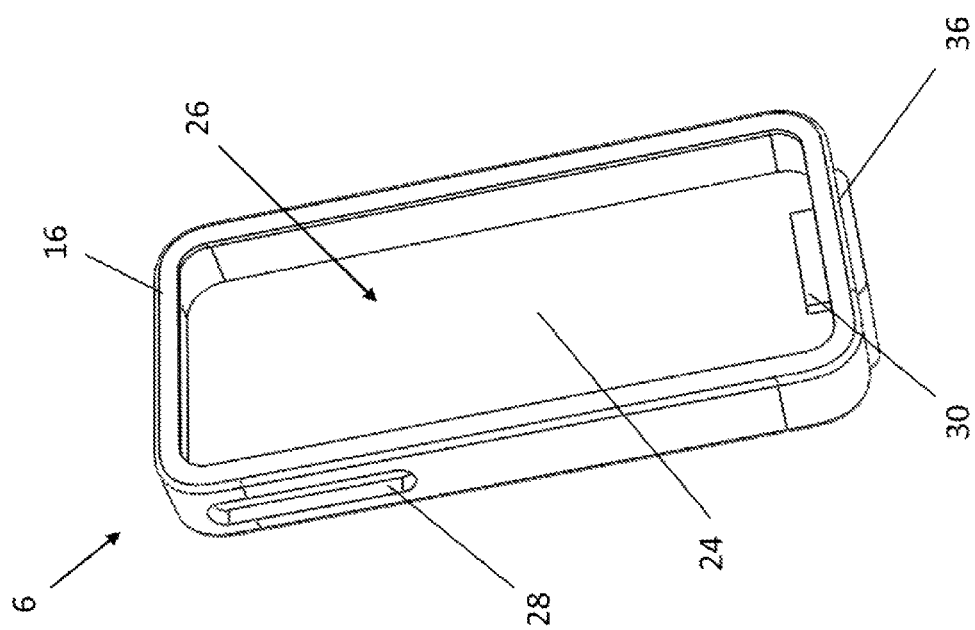
FIG. 1 is a front perspective view of a variation of the injector device.
Figure 2:
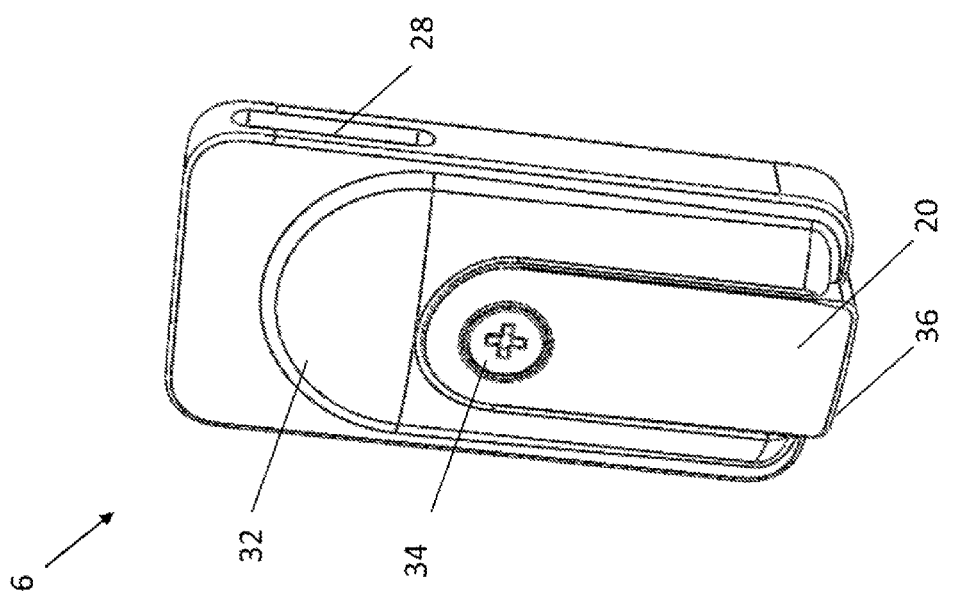
FIG. 2 is a rear perspective view of a variation of the injector device.
Figure 3:
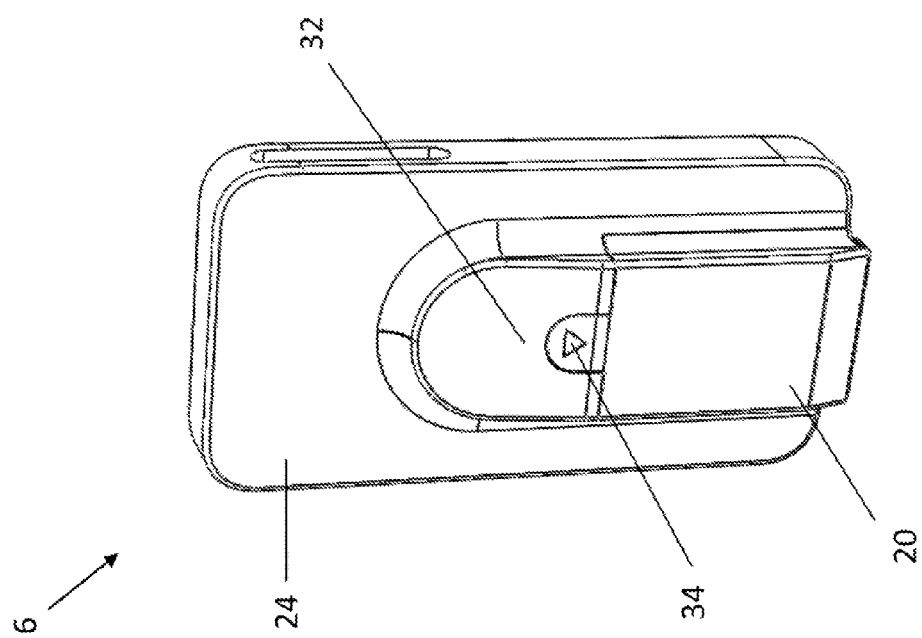
FIG. 3 is a rear perspective view of a variation of the injector device.

FIGS. 1 through 3 illustrates that an injector device can have a device case or frame 6. The injector device can have a cartridge 14 attached to or integrated with the device frame 6. The cartridge 14 can be an auto-injector and can operate within the injector device or be removed from the remainder of the device and used in a stand-alone fashion. The cartridge 14, with or without the remainder of the injector device, can inject a fluid subcutaneously or percutaneously into a patient's body, for example intravascularly, intramuscularly, or into adipose tissue. The cartridge 14 can contain a trigger 8, trigger lever 22, needle 2, reservoir, fluid, and safety system, as described herein.

The injector device can inject a fluid subcutaneously or percutaneously into a patient's body, for example intravascularly, intramuscularly, or into adipose tissue. The injector device can be used to treat anaphylactic shock (e.g., as an allergic reaction), diabetes, or combinations thereof. The fluid can be a medication or therapeutic fluid, and/or a diagnostic fluid.

The injector device frame 6 can have a rim 16. The device frame 6 can have a rear panel 24 integrated with or attached to the rim 16. The device frame 6 can be rigid or flexible. For example, the rear panel 24 and/or the rim 16 can be made from a rigid plastic and/or metal and/or can be made from an elastic rubber.

The rim 16 can be rigid or flexible. For example, the rim 16 can be hard plastic and/or elastic rubber. The rim 16 can define a front port 26 of the device frame 6. The front port 26 can be rectangular or have a rounded rectangular configuration. The rim 16 can have a side port 28 in the lateral side of the rim 16. The side port 28 can have a rectangular or rounded rectangular configuration.

FIG. 1 illustrates that that device frame 6 can have a portable electronics connector, such as a phone connector 30. The phone connector 30 can form a power and/or data connection between the phone connector 30 and the phone 4 (or other portable electronic device). The device frame 6 can have operational electronics, such as one or more switches, circuits, such as printed circuit boards, processors, sensors (e.g., optical, RF), input devices or electronic controls (e.g., buttons, levers, touchscreens), output devices (e.g., display screens, LEDs), or combinations thereof. The operational electronics can be embedded in the frame 6 and/or on the surface of the frame 6.

FIGS. 2 and 3 illustrate that the device frame 6 can have a cartridge pocket 32. The cartridge pocket 32 can be a hollow volume in the rear panel 24. The cartridge pocket 32 can extend outwardly (i.e., in a rear direction) from the plane of the remainder of the rear side of the rear panel 24, as shown, and/or inwardly (i.e., in a front direction) from the plane of the remainder of the front side of the rear panel 24. FIG. 2 illustrates that the cartridge pocket 32 can have a semi-circular configuration at the top of the pocket 32. FIG. 3 illustrates that the cartridge pocket 32 can have a squared-off, rectangular configuration at the top of the pocket 32.

The frame 6 can have a trigger switch cover or trigger lever cover 20. The trigger lever cover 20 can cover a portion of the cartridge pocket 32. The trigger lever cover 20 can be slidably attached to and/or be removably attached (e.g., by a snap-fit) to the remainder of the frame 6. The trigger lever cover 20 can have or be attached to a trigger lever cover release button 34. The trigger lever cover release button 34 can be configured to release the attachment of the trigger lever cover 20 to the remainder of the device frame 6. The trigger lever cover release button 34 can be depressed and/or used as a finger grip (e.g., as an indented and/or ridgedly or knurledly textured portion of the trigger lever cover 20).

The bottom of the cartridge pocket 32 and/or bottom terminal portion of the rim 16 or rear panel 24 can form a stand 36. The stand 36 can extend down beyond the remainder of the device frame 6. The stand 36 can have a flat bottom surface. The stand 36 can be slightly concave, for example to fit against the curvature of the thigh or upper arm of the injection recipient.

The device frame 6 can have an external power and/or data connectors. The power and/or data connectors can be in the stand 36, the lateral sides of the frame 6, or combinations thereof. The power and/or data connectors can be configured to receive or deliver power and/or data. The power and/or data connectors can be connected to the phone connector 30. For example, the power and/or data connector can transmit power to and/or from the phone 4 through the phone connector 30. The phone 4 can have a phone battery that can be charged while the device frame 6 is on the phone 4. The device frame 6 may contain a frame battery. The frame battery can be charged from the power and/or data connector and/or from the phone battery. The phone battery can be charged from the frame battery.

Figure 4:
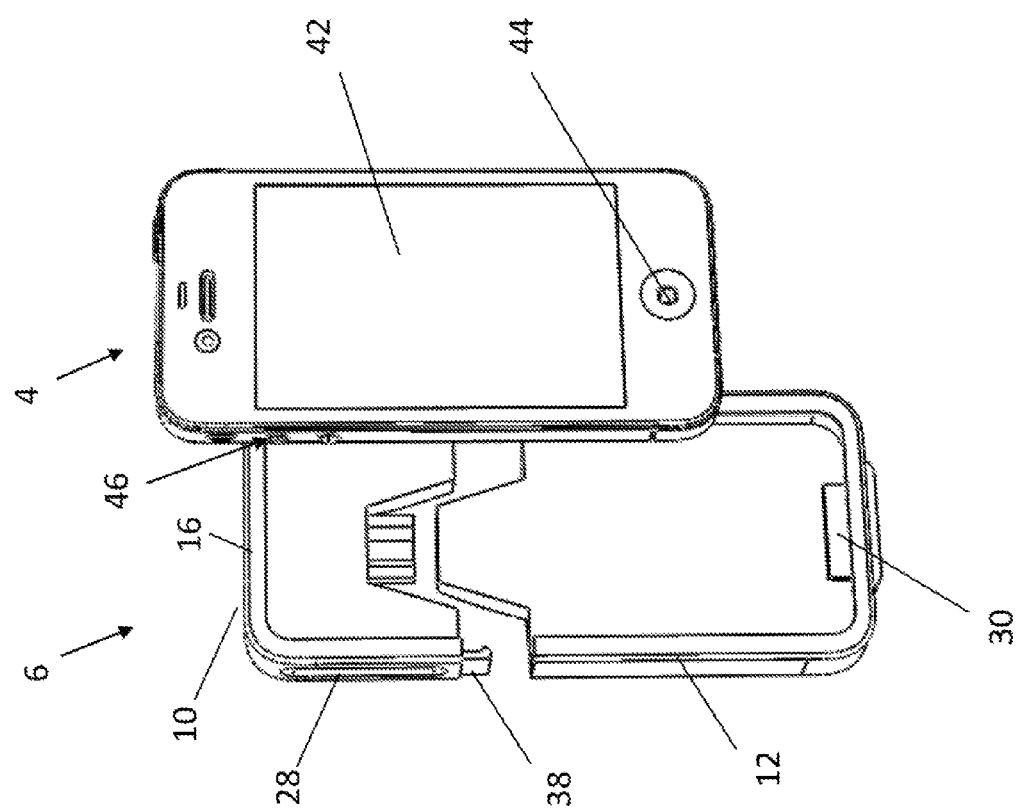
FIG. 4 is a front perspective view of a variation of the injector device separated from a phone 4.

FIG. 4 illustrates that the device frame 6 can have one, two or more releasably attached frame 6 components or structural bodies. For example, the frame 6 can have a frame top 10 releasably attached to a frame bottom 12. The frame top 10 (as shown) and/or bottom 12 can have one or more connecting tabs 38 extending away from the remainder of the frame top 10 and/or bottom 12 and to the other (i.e., the frame bottom 12 and/or top 10, respectively). The frame top 10 and/or bottom 12 can have correlating receiving configurations, such as tab holes, slots, guides, rails, ridges, notches, divots, pockets, or combinations thereof, to receive and relasably attach to the connecting tabs 38.

The injector device can be attached to or integrated with one or more portable electronics device, such as a phone 4, tablet computer, portable music player (e.g., mp3 player), personal data assistant (PDA), or combinations thereof. An injector assembly 17 can be the portable electronics device assembled with the injector device. The phone 4 can be a smartphone, cellular phone, landline phone, or combinations thereof. The phone 4 can be connected to the phone connector 30. The phone 4 can transmit and receive data and/or power through the phone connector 30.

The phone 4 can have phone input/output elements, such as a phone screen 42 (e.g., a touchscreen) and phone front controls 44 (e.g., buttons) on the front of the phone 4. The phone screen 42 and/or phone front controls 44 can be accessed through the front port 26 of the device frame 6, and/or covered by the rim 16. The phone 4 can have phone side controls 46 on one or more lateral sides of the phone 4. The phone side controls 46 can be accessed through the side ports 28 and/or covered by the rim 16. The phone 4 can have a replaceable and/or rechargeable battery that can supply power to the phone 4 and/or through the phone connector 30. The phone 4 can have wired or wireless connections to communicate with one or more networks (e.g., the internet, the PSTN).

Figure 5:
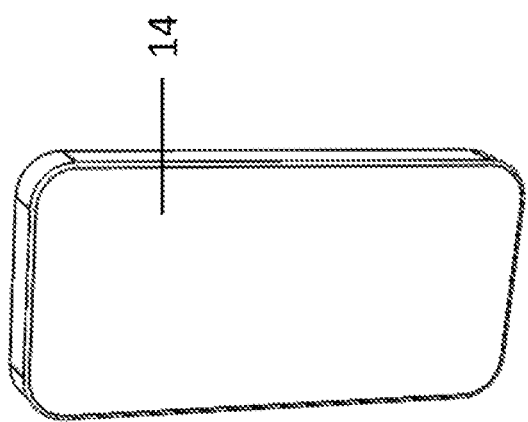
FIG. 5 is a front perspective view of a variation of the cartridge 14.

FIG. 5 illustrates that the injector device can have a cartridge 14. The cartridge 14 can be attached to or integral with the device frame 6. The cartridge 14 can have a rigid outer structure or case. The cartridge 14 can have a trigger 8 within the case. The trigger 8 can be slidably attached to the remainder of the cartridge 14. The trigger 8 can have or be attached to a needle 2. The needle 2 can be spring-loaded or otherwise attached to a spring. The needle 2 can be in the trigger 8. The needle 2 can be locked into place by the trigger 8. When the trigger 8 is activated, the needle 2 can be released and the spring can eject a length of the needle 2 out of the remainder of the cartridge 14, such as out of the case and/or out of the trigger 8, and hold a length of the needle 2 (e.g., at the terminal proximal end of the needle 2).

The cartridge 14 can have a contained volume, such as a bladder, reservoir, channel, ampoule, or combinations thereof. The contained volume can be in fluid communication with the needle 2. The contained volume can be held under pressure and/or be subject to positive pressure when the trigger 8 is activated. The contained volume can have a fluid, such as a medication such as epidephrine, insulin, vaccines, antidotes, dihydroergotamine, hydrocortisone sodium, steroids, zoledronic acid, pramlintide, exenatide, sodium bicarbonate, norepinephrine, atropine, dopamine, dobutamine, or combinations thereof.

The contained volume can be surrounded on the phone-side (e.g., the front) and/or all sides by a thermal insulation. The case can be opaque, translucent and/or transparent (e.g., the case can be partially opaque and have a transparent or translucent window into the contained volume, for example to check volume level).

The cartridge 14 can have a data carrying label, such as an RFID tag, bar code, or combinations thereof. The label can contain data such as fluid type or contents, expiration and/or manufacturing dates, manufacturing lot numbers, volume, or combinations thereof.

Figure 6:
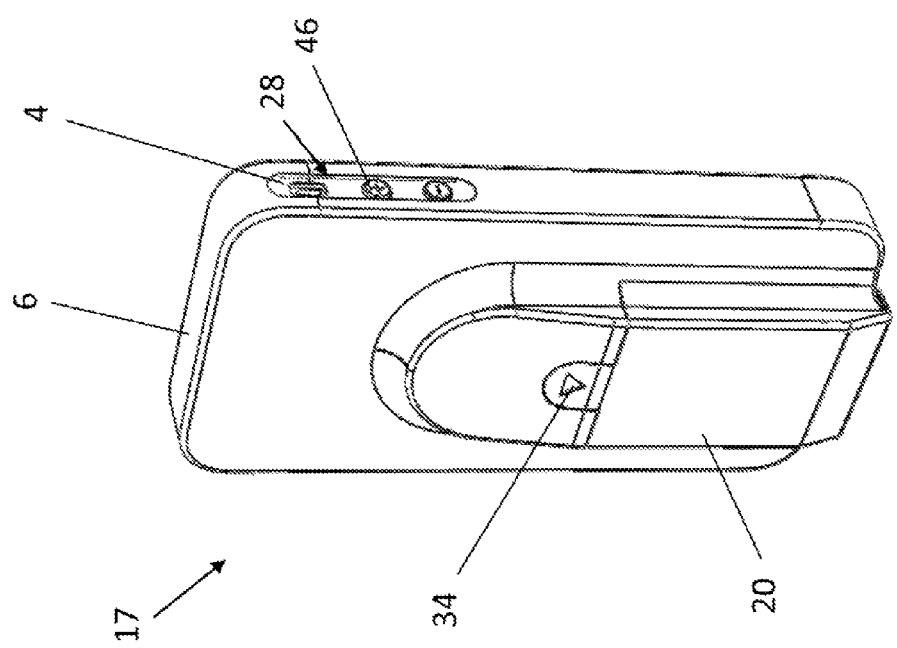
FIG. 6 is a side perspective view of a variation of the injector device attached to a phone 4.

FIG. 6 illustrates that the phone 4 and cartridge 14 can be in the device frame 6. For example, the frame top 10 and frame bottom 12 can be slid over the phone 4 and the cartridge 14, and the frame top 10 can be attached to the frame bottom 12, for example with the connecting tabs 38.

The phone side controls 46 visible and accessible through side port 28. The phone screen 42 and phone front controls 44 can be visible and accessible through the front port 26.

Figures 7, 8:
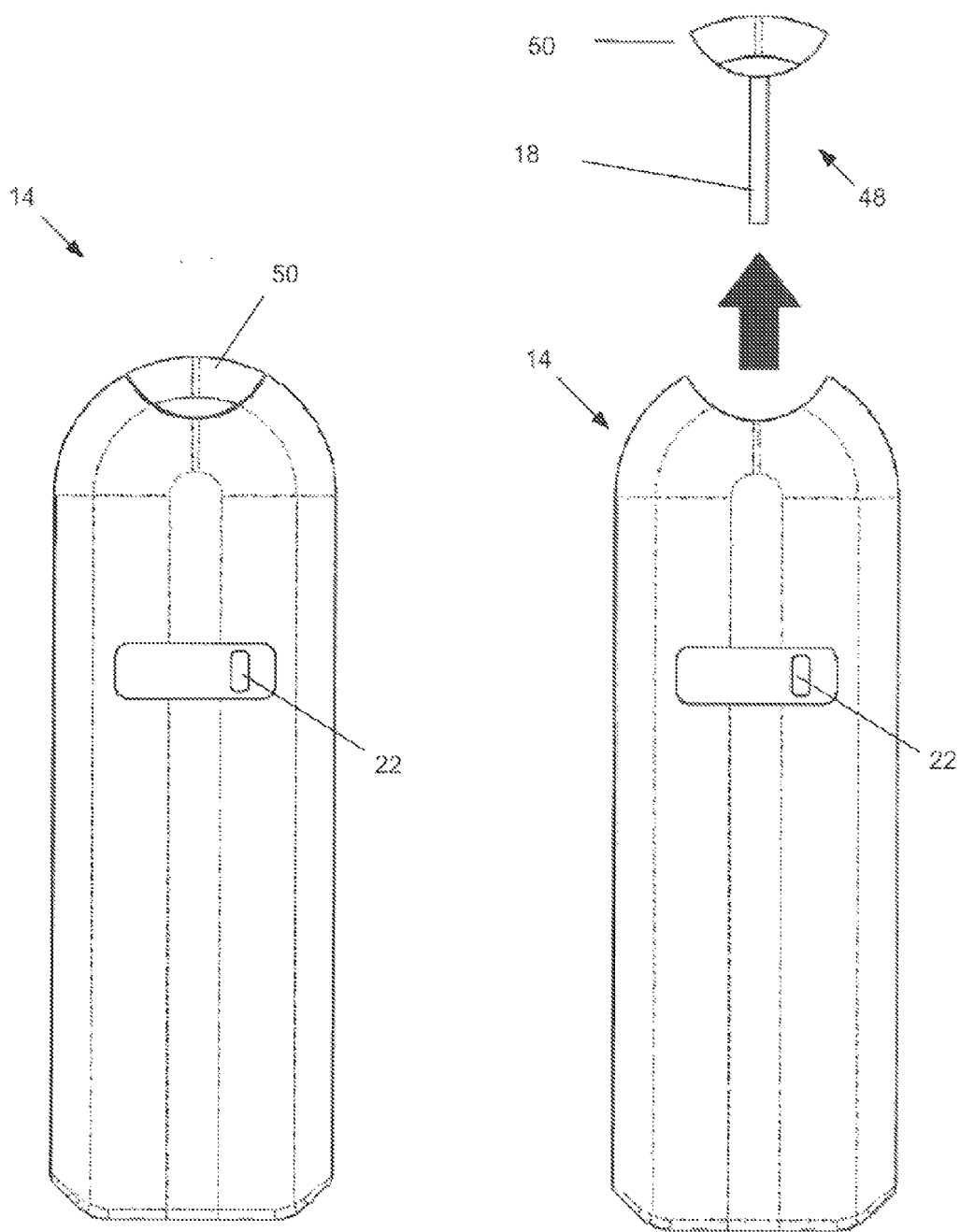
FIG. 7 illustrates a variation of the cartridge 14.
FIG. 8 illustrates a variation of a method of removing the safety tab 18 from the cartridge 14.

FIG. 7 illustrates that the cartridge 14 can have a switch, such as a trigger button or trigger lever 22. The trigger lever 22 can be configured to release the trigger 8 so the trigger 8 can emerge from the remainder of the cartridge 14. The trigger 8 can be spring-loaded. The cartridge 14 can have a safety 48 having a safety cap 50. The safety 48 can be attached, for example within the cartridge 14, to the trigger lever 22. With the safety 48 in the cartridge 14, the safety 48 can interference fit with the trigger lever 22 and/or trigger 8 to prevent the trigger lever 22 from being manipulated to release the trigger 8.

FIG. 8 illustrates that the safety cap 50 can be pulled out from the cartridge 14, as shown by the arrow. The safety cap 50 can be pulled away from the cartridge 14 before or after the cartridge 14 is placed into the device frame 6. The safety 48 can have a safety tab 18 extending from the safety cap 50. The safety tab 18 can interference fit with the inside of the trigger lever 22. The safety tab 18 can be in a cartridge port 52 at the top end of the cartridge 14.

Figures 9, 10:
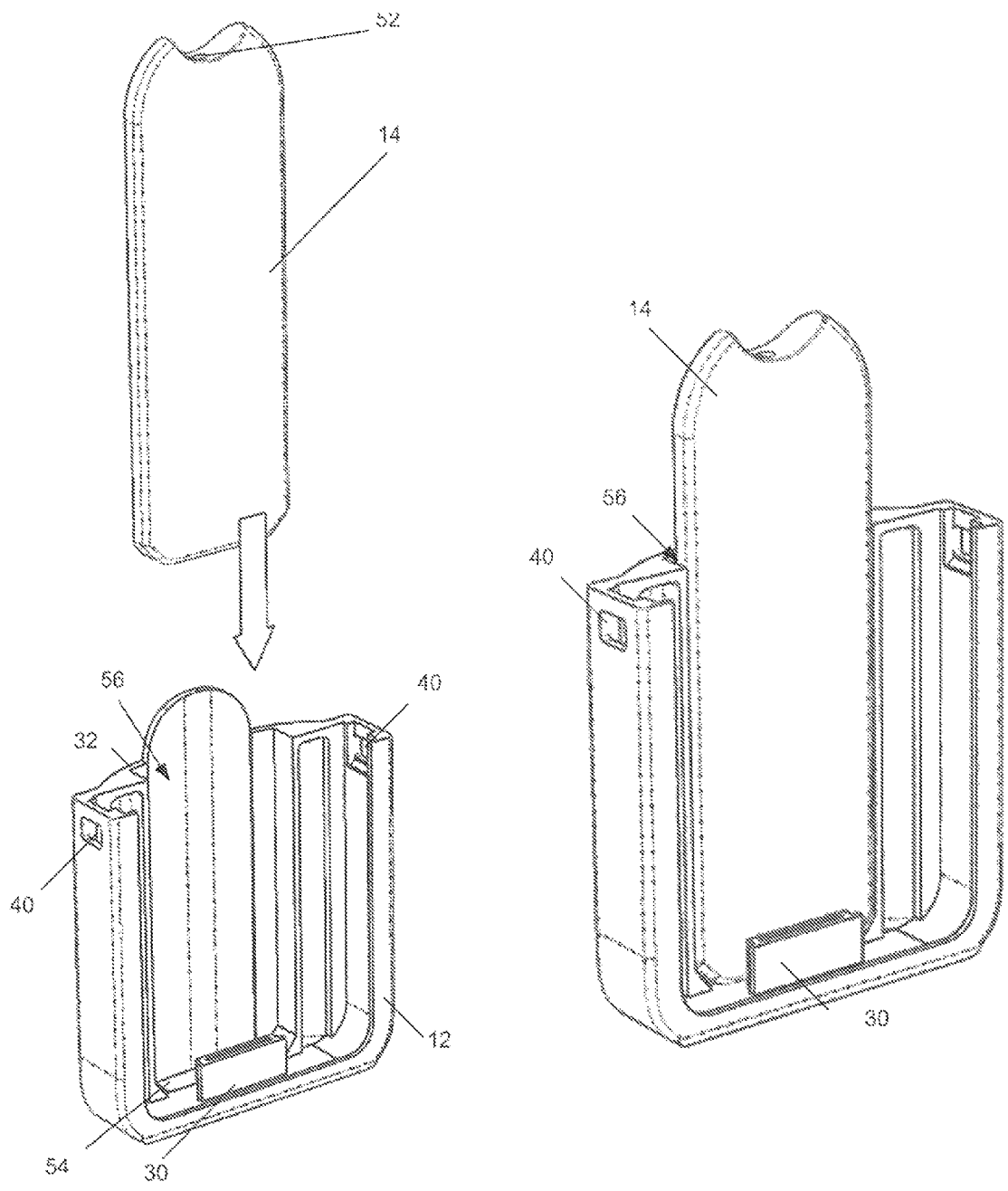
FIGS. 9 through 14 illustrate a variation of assembling a variation of the injector device onto a phone 4.

FIG. 9 illustrates that the frame bottom 12 can have a frame trigger port 54. The frame trigger port 54 can be an opening in the frame 6 large enough for the trigger 8 to pass through and/or be accessed.

The cartridge pocket 32 in the frame bottom 12 can have a cartridge bottom slot 56. The cartridge bottom slot 56 can be recessed in the frame pocket. The cartridge bottom slot 56 can have guides or rails, for example to align and hold the cartridge 14. The cartridge bottom slot 56 can have a snap or latch, for example to releasably attach to the cartridge 14. The bottom of the cartridge bottom slot 56 can be the frame trigger port 54. The cartridge 14 can be translated, as shown by the arrow, into the cartridge bottom slot 56.

The cartridge 14 can have one or more cartridge ports 52, for example at the top terminal end of the cartridge 14. The cartridge port 52 can receive the safety tab 18 and/or access the contained volume. For example, the contained volume of the cartridge 14 can be filled or refilled through a needle 2 inserted through the cartridge port 52. The cartridge port 52, and/or a port into the contained volume can be self-sealing, such as with an elastomeric polymer seal.

FIG. 10 illustrates that the cartridge 14 can be seated in the cartridge bottom slot 56. The cartridge 14 can be positioned with respect to the frame bottom 12 so the trigger 8 is adjacent to and aligned with the frame trigger port 54. The cartridge 14 can be in contact with the frame bottom 12. The cartridge 14 can be held or pressed between ridges, rails, or in a slot in the frame bottom 12.

Figure 11:
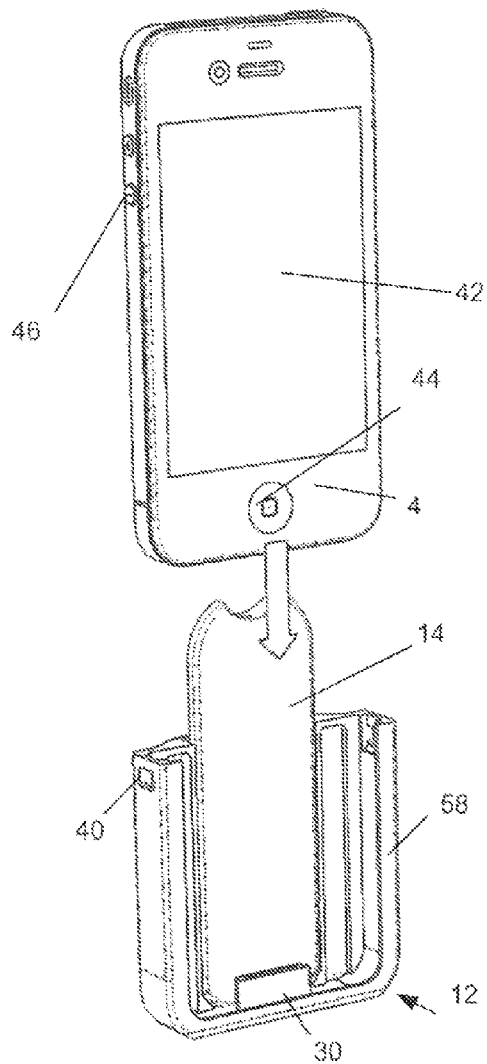

FIG. 11 illustrates that the phone 4 can be slidably translated into the frame bottom 12, as shown by the arrow. Alternatively, or in addition, the rim 16, for example for a variation of the frame 6 having an elastic rim 16, can be deformed and stretched around the phone 4. The bottom rim 58 can guide the phone 4 into the bottom frame. The cartridge 14 can be held or pressed between the phone 4 and the frame bottom 12.

Figure 12:
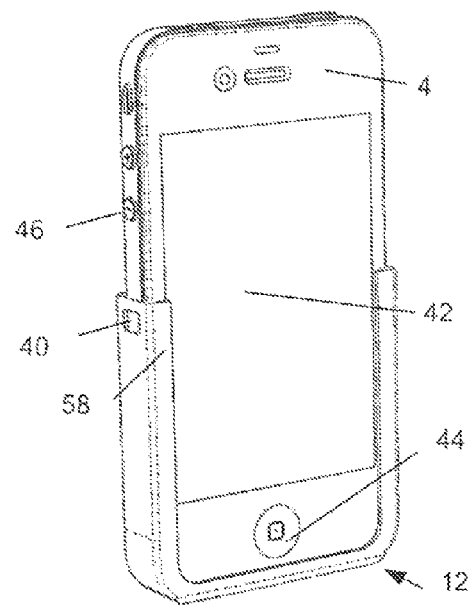

FIG. 12 illustrates that when the phone 4 is slid into the frame bottom 12, the phone connector 30 can plug into the phone 4 and/or the phone 4 can plug into the phone connector 30. The phone connector 30 can form a data and/or power connection and communication between the phone 4 and the operational electronics of the device frame 6. Instead or in combination with the phone connector 30, the operational electronics of the frame 6 can be in wireless data and/or power communication with the phone 4, such as by RF, Bluetooth, inductive power or data transfer, or combinations thereof.

The rim 16 can hold the phone 4 and prevent phone 4 from translating forward with respect to the frame 6.

Figure 14:
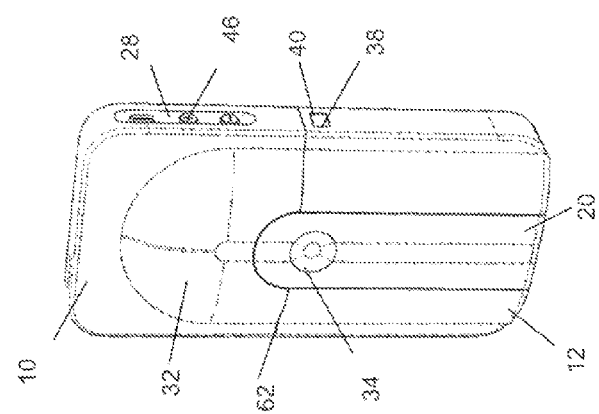
Figure 13:
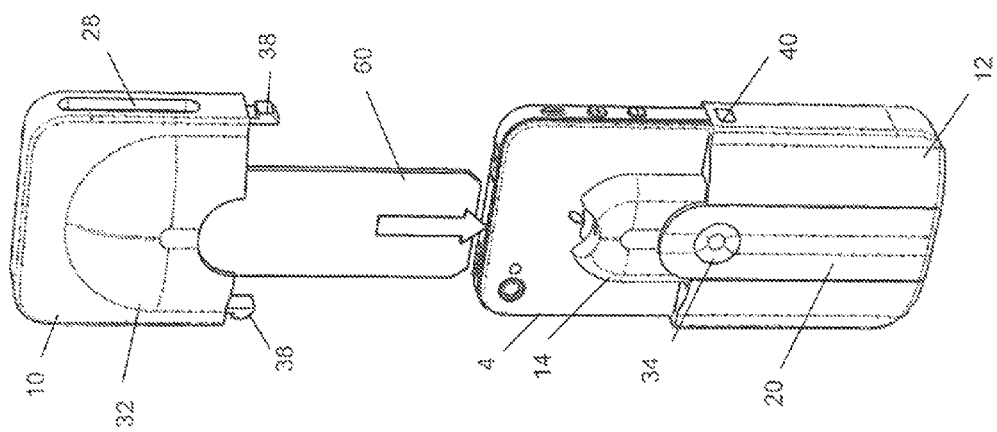

FIG. 13 illustrates that the frame top 10 can be translated down toward the frame bottom 12, as shown by the arrow. A thermal insulating plate 60 or heat shield can slide between the cartridge 14 and the phone 4. The thermal insulating plate 60 can be made from ceramic, styrofoam, plastic, rubber, PTFE (e.g., Teflon), vinyl, laminates, epoxy/fiberglass, glass, paint, or combinations thereof. The thermal insulating plate 60 can be fixedly attached to the frame top 10, frame bottom 12 or front of the cartridge 14. The thermal insulating plate 60 can be separate from the other components and slid between the cartridge 14 and the phone 4 into the frame top 10 and bottom during assembly 17. For example, the thermal insulating plate 60 can be made from polyurethane and can have a coefficient of thermal conductivity k from about 0.020 W/mK to about 0.40 W/mK, for example about 0.033 W/mK. FIG. 14 illustrates that the frame top 10 can be attached to the frame bottom 12. For example, the connecting tabs 38 can deform and detachably fit into the tab holes. The frame top 10 and frame bottom 12 can cover the rear of the cartridge 14 and/or the rear of the phone 4. The frame top 10 can meet the frame bottom 12 at a frame seam 62.

The tabs can be depressed and the top frame can be separated from the bottom frame. The cartridge 14 can then be replaced. For example an empty cartridge 14 can be replaced with a full cartridge 14 and then the top frame can then be reattached to the bottom frame.

Figure 15:
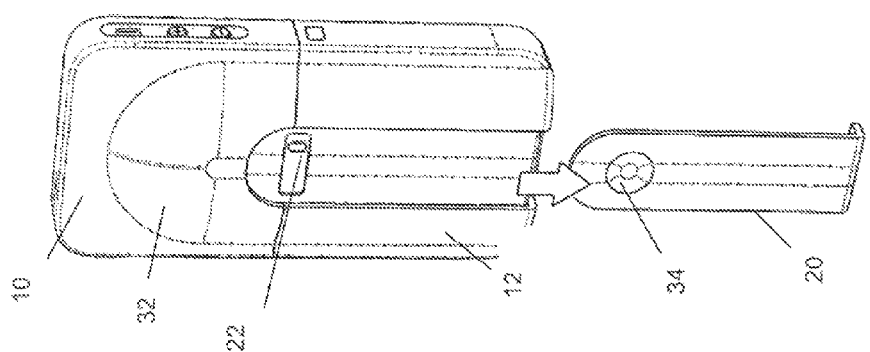
FIGS. 15 through 19 illustrate a variation of a method for deploying the trigger 8.

FIG. 15 illustrates that the trigger lever cover release button 34 can be depressed to release (e.g., unlatch, unlock, or combinations thereof) the trigger lever cover 20 from the remainder of the frame bottom 12. The trigger lever cover 20 can be translated or slid, as shown by arrow, off the frame 6, exposing the trigger lever 22.

Figure 16:
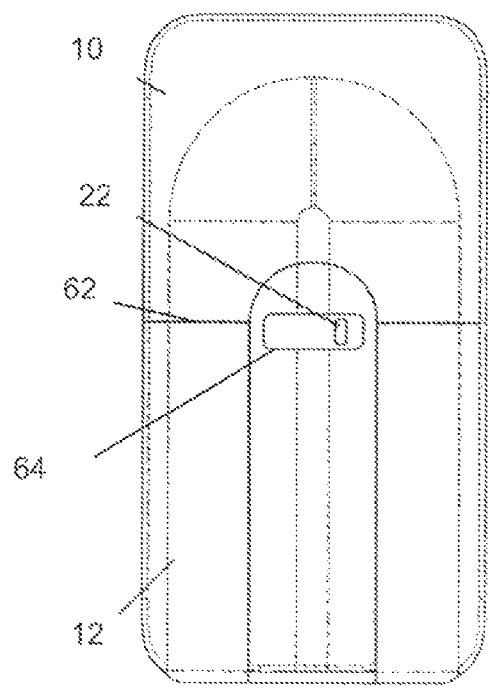
Figure 17:
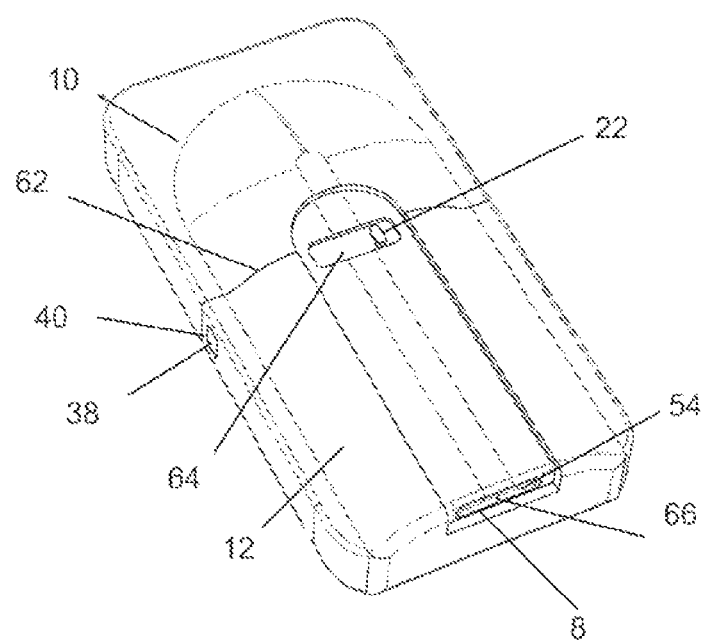

FIGS. 16 and 17 illustrate that the trigger lever can be slidably positioned in a lever window 64. The trigger lever and the lever window 64 can be exposed with the trigger lever cover 20 removed. The trigger lever can be in an unreleased position. For example, the trigger lever can be on the right side of the lever window 64 as shown.

The trigger 8 can be recessed within the frame bottom 12. The trigger 8 can be aligned with and adjacent to the frame trigger port 54) when the trigger lever is in an unreleased position. The bottom terminal end of the trigger 8 can be in the frame trigger port 54 (as shown) when the trigger lever is in an unreleased position. The trigger 8 can have a needle port. The needle port 66 can be at the terminal end of a needle channel. The needle 2 can be slidably located within the needle channel.

Figure 18:
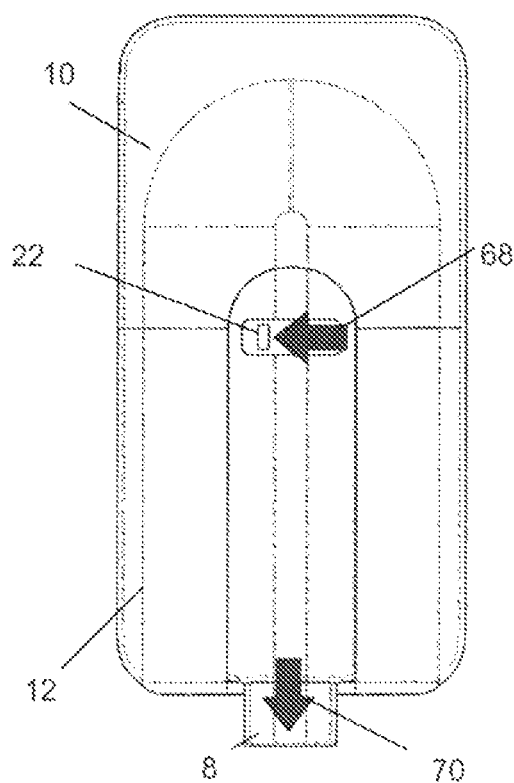
Figure 19:
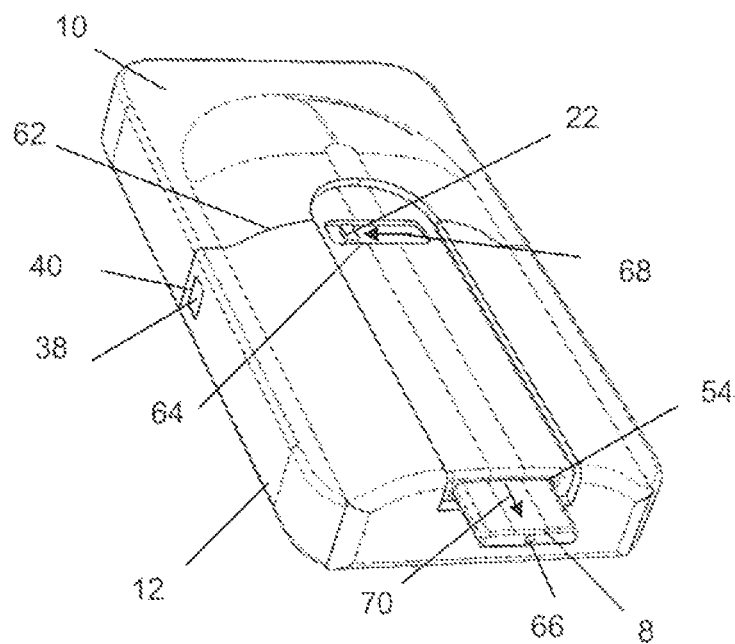

FIGS. 18 and 19 illustrate that the trigger lever can be translated, as shown by the arrow. For example, the trigger lever can be pushed or slid along the lever window 64 from the right to the left. The trigger lever translation can activate the trigger 8 to be translated, as shown by the arrow. For example, the trigger 8 can be spring-loaded and the lever translation 68 can release a latch or lock holding the trigger 8 in the device frame 6.

The trigger 8 can exit (i.e., translate out of) and extend from the frame trigger port 54. The top end of the trigger 8 can be retained within and held be the device frame 6 and/or cartridge 14. The trigger 8 can be part of the cartridge 14. The trigger 8 can be slidably attached to the remained of the cartridge 14.

Figure 20:
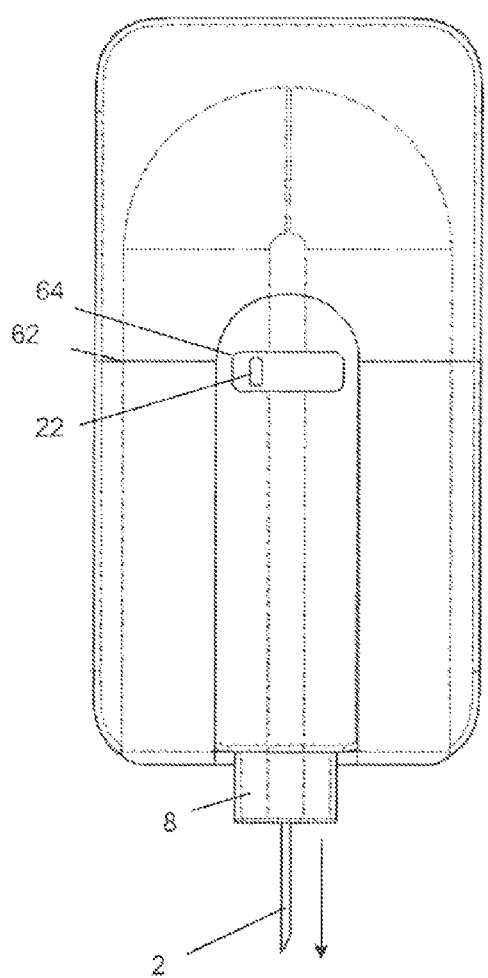
FIG. 20 is a rear view of a variation of the injector device with the trigger 8 and needle 2 deployed.
Figure 21:
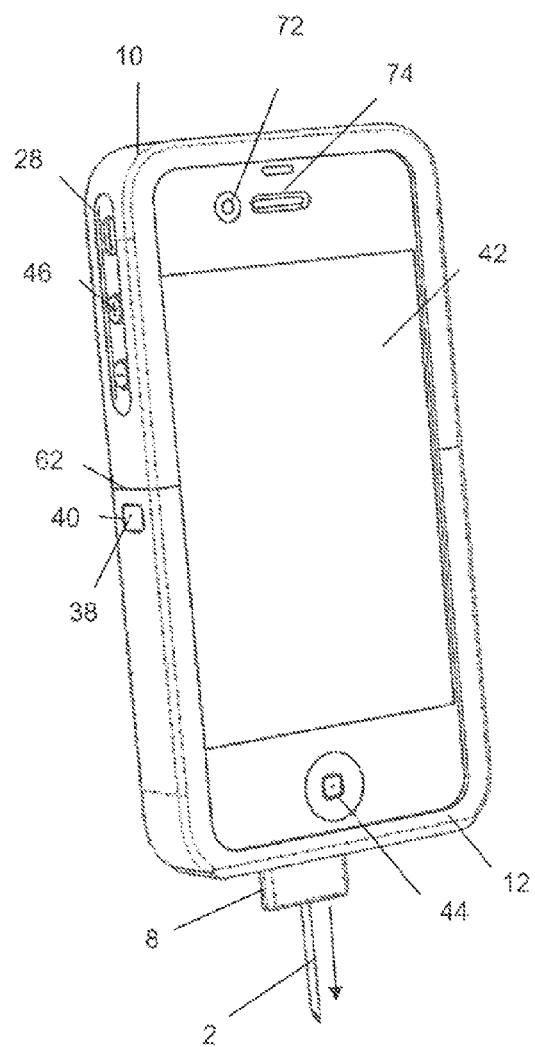
FIG. 21 is a front side perspective view of a variation of the injector device and a phone 4 with the trigger 8 and needle 2 deployed.

FIG. 20 illustrates that the needle 2 can exit and extend from the needle port 66 in the trigger 8, as shown by the arrow. For example, the needle 2 can be spring-loaded and can be pushed out of the needle port 66 when the trigger 8 is activated. The trigger 8 can be activated by pressing up on the trigger 8 (i.e., toward the remainder of the cartridge 14 and device frame 6). For example, the device frame 6 and trigger 8 can be pressed into an arm, leg, abdomen or buttock, activating the trigger 8, and deploying the needle 2 into the tissue of the arm, leg, abdomen or buttock. The needle 2 can be retained by a safety catch when in the trigger 8 or cartridge 14. Activating the trigger 8, for example by pressing on the trigger 8, can release the safety catch. The proximal or top terminal end of the needle 2 can be held and retained by the trigger 8, and/or cartridge 14, and/or device frame 6.

The needle 2 can be in fluid communication with the contained volume. When the trigger 8 is activated and/or when the needle 2 exits the needle port, pressurized fluid from within the contained volume can be forced through the extended needle 2. The needle 2 can inject, infuse or otherwise deliver the contents of the contained volume into the tissue. For example, the needle 2 can deliver the contained volume contents subcutaneously, percutaneously, intra-vascularly, or combinations thereof.

When the trigger 8 is activated, a reservoir plunger spring and/or needle spring can be released and press on a reservoir plunger to push the reservoir and needle 2 down. The needle 2 can be fully deployed when the reservoir hard stops against the internal (i.e., inside of the frame 6) side of the trigger 8. The plunger spring and/or needle spring can then continue pressing on the plunger to force the fluid from the reservoir through the needle 2 and into the target site, for example into subcutaneous tissue.

The device frame 6 can communicate to the phone 4 the actions of the trigger release, and/or needle 2 deployment, and/or delivery of the contents of the contained volume are delivered through the needle 2. The phone camera 72 (e.g., to take pictures of the surroundings or the patient) and/or the phone speaker 74 (e.g., to announce instructions or a medical emergency to the patient or passersby) can be automatically activated based on the actions communicated to the phone 4 by the device frame 6 through the phone connector 30 and/or wirelessly.

Figure 22:
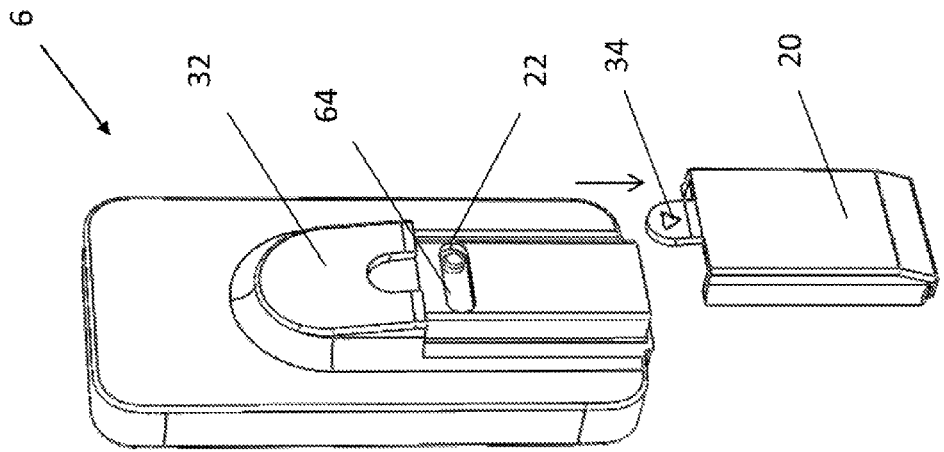
FIG. 22 is a rear side perspective view of a variation of the injector device with the trigger lever cover 20 removed.

FIG. 22 illustrates that the trigger lever cover 20 can be removed from the device frame 6, as shown by the arrow. The trigger lever cover 20 can be pulled off downwardly or rearwardly. The trigger lever can have a circular grip, as shown in FIG. 22, or a rectangular grip, as shown in FIGS. 7, 8, and 15-20.

Figure 23:
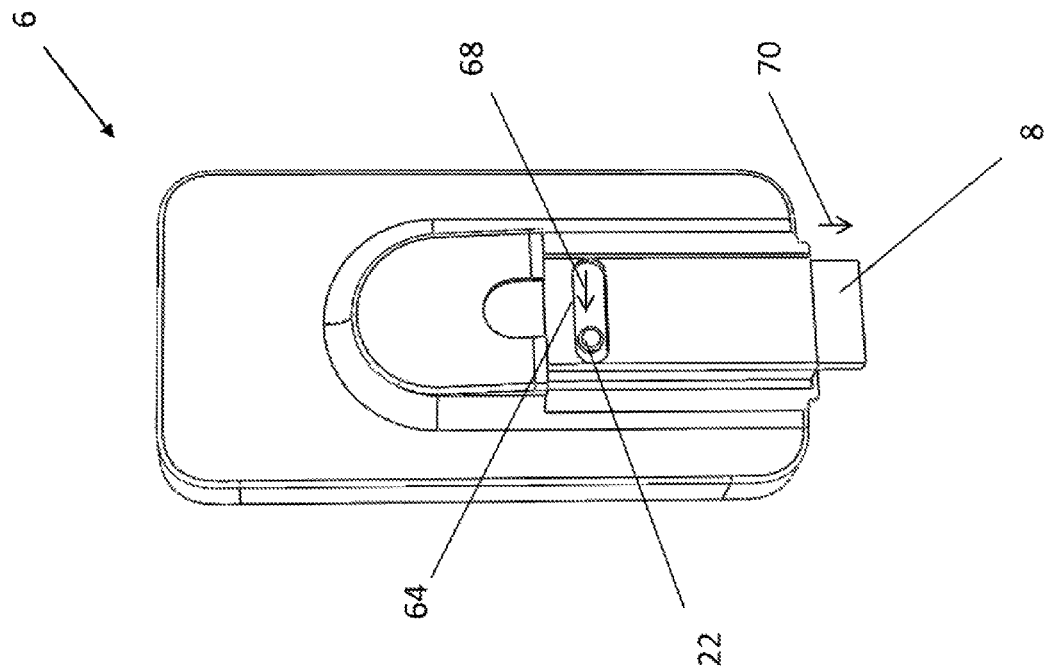
FIG. 23 is a rear side perspective view of a variation of the injector device with the trigger 8 deployed.

FIG. 23 illustrates that the trigger lever can be translated from the right to the left sides of the trigger lever window 64, as shown by the arrow. The trigger 8 can then be translatably deployed from the cartridge 14 and/or frame 6, as shown by arrow.

Figure 24:
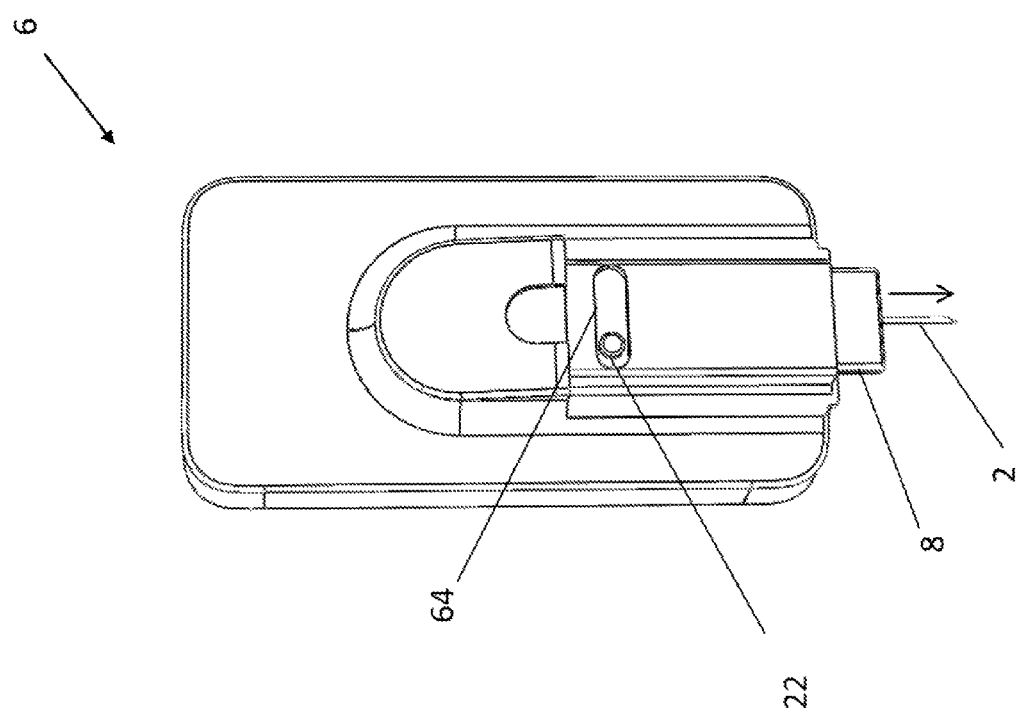
FIG. 24 is a rear side perspective view of a variation of the injector device with the trigger 8 and needle 2 deployed.

FIG. 24 illustrates that when the trigger 8 is activated, the needle 2 can be deployed from the trigger 8, as shown by arrow. The needle 2 can then deliver to a target site of tissue the contents of the contained volume under pressure.

Figure 25:
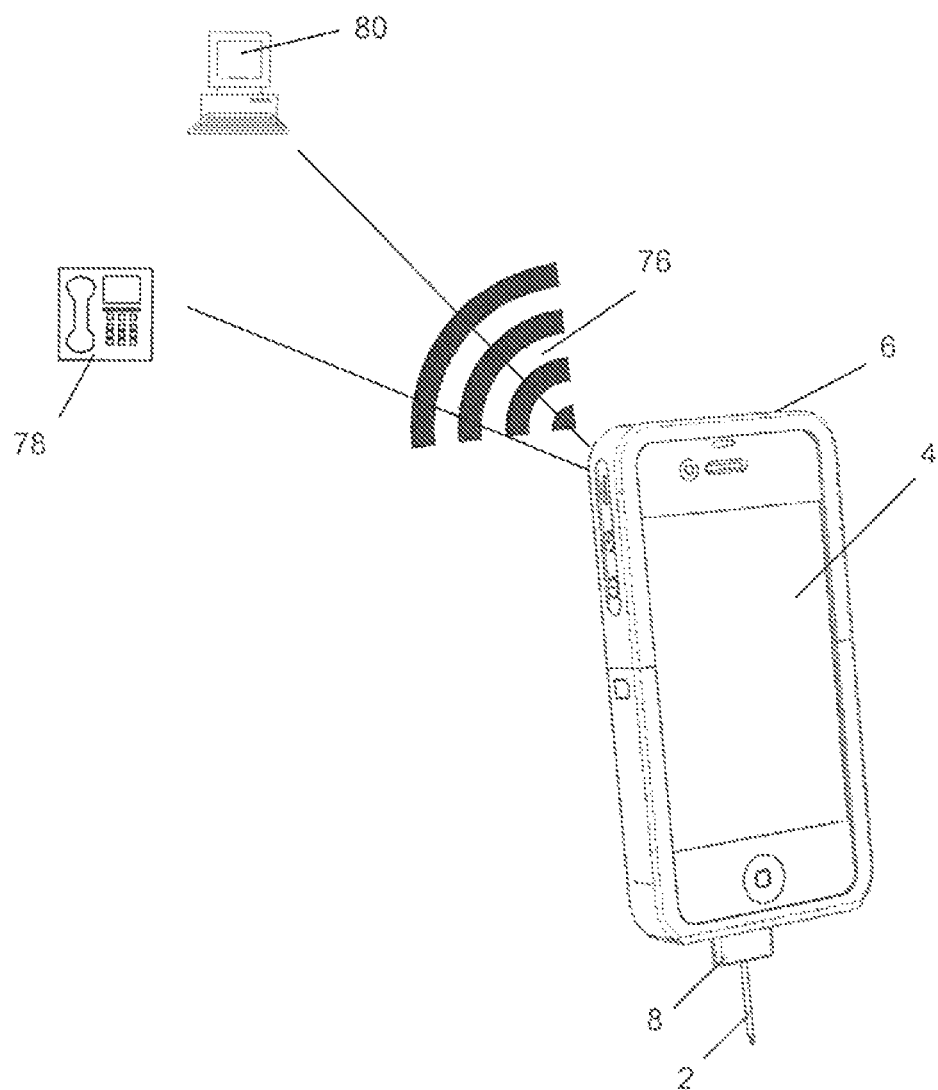
FIG. 25 is a front side perspective view of a variation of the injector device transmitting and/or receiving wireless information.

FIG. 25 illustrates that the when the phone 4 receives communication from the device frame 6 that actions of the trigger release, and/or needle 2 deployment, and/or delivery of the contents of the contained volume are delivered through the needle 2 occur, the phone 4 can communicate data through a wired or wireless signal 76 to a call, text, SMS, or MMS recipient's phone 78, computer 80, computer network, or combinations thereof. The phone 4 can communicate, for example, by uploading the data to a network, calling emergency medical services with an automated message and sending the GPS location of the phone 4, calling or texting individuals on a contact list, or combinations thereof.

The device frame 6 can send data to the phone 4 through the phone connector 30 of the actions such as trigger release/actuation, needle 2 deployment/translation, delivery of the reservoir contents/injection, and of fluid (e.g., medication) level or quantity in the contained volume in the cartridge 14, fluid (e.g., medication) level or quantity delivered in the injection, fluid (e.g., medication) or cartridge 14 age since manufacturing, fluid (e.g., medication) instantaneous, maximum, minimum, and average temperatures, fluid (e.g., medication) viability (e.g., a formula that can include the temperatures experiences by the fluid and the age of the fluid and the type of fluid), fluid (e.g., medication) type, brand, or combinations thereof.

The device can have an optical or RFID sensor configured to detect a bar code or RFID tag on the cartridge 14 identifying the contents and can transmit the data to the phone 4.

Phone 4 can transfer any medication or use data to a network, for example to a server and/or place a call, SMS, MMS, instant message or combinations thereof, such as to one or more contacts in a contact list (e.g., emergency medical services ("911 service"), primary healthcare provider, family, friends).

The phone 4 can receive information, such as recall information regarding the medication or other information (e.g., update instructions for use, advertisements) targeted to users of the medication or device. Phone 4 can receive and transmit data to the electronics in the device frame 6, such as software updates.

U.S. Pat. No. 7,390,319 is incorporated by reference herein in its entirety. Any or all features of the cartridge 14 and/or auto-injector and/or other elements disclosed herein can be the same as those disclosed in U.S. Pat. No. 7,390, 319.

It is apparent to one skilled in the art that various changes and modifications can be made to this disclosure, and equivalents employed, without departing from the spirit and scope of the invention. Elements of systems, devices and methods shown with any embodiment are exemplary for the specific embodiment and can be used in combination or otherwise on other embodiments within this disclosure.

I claim:

1. An injector system comprising:
   a phone;
   a phone case comprising a reservoir, wherein the phone case further comprises a heat shield, a needle in fluid communication with the reservoir, a trigger and a spring; and
   wherein the phone case is configured to deform during attachment or detachment to the phone, and wherein the heat shield is between the phone and the reservoir, wherein the reservoir comprises a fluid; and
   wherein the trigger has a first configuration inside of the phone case and a second configuration extending from the phone case further comprising at least one configuration of the system the needle is at least partially inside of the trigger.

2. The system of claim 1, wherein the heat shield has a thermal conductivity k from 0.020 W/mK to 0.40 W/mK.

3. The system of claim 1, wherein the spring is positioned against the trigger, and wherein the spring is in a compressed configuration when the trigger is in the first configuration, and wherein the spring is in an extended configuration when the trigger is in the second configuration.

4. The system of claim 1, wherein the trigger and the needle extend from the same end of the phone case.

5. The system of claim 1, wherein the needle is configured to slidably translate within the trigger.

6. The system of claim 1, wherein the reservoir comprises a fluid, and where the fluid comprises a medication.

7. An injector system comprising:
   a mobile phone;
   a phone case comprising a reservoir, a needle in fluid communication with the reservoir, and a trigger, wherein the reservoir comprises a fluid, and wherein the needle has a first configuration inside of the phone case and a second configuration extending from the phone case, and wherein the phone case is configured to be removably snapped-in to the phone; and
   a heat shield located between the reservoir and the phone; wherein in at least one configuration of the system the needle is at least partially inside of the trigger.

8. The system of claim 7, wherein the needle is spring-loaded in the case.

9. The system of claim 7, wherein the reservoir comprises a fluid, and where the fluid comprises epinephrine and/or insulin.

10. The system of claim 7, wherein the reservoir and the heat shield are between the phone case and the phone.

11. The system of claim 7, wherein the phone case further comprises a frame bottom and a frame top, and wherein the frame bottom is configured to releasably attach to the frame top.

12. The system of claim 7, wherein the phone case further comprises a data communication element comprising at least one of a plug or an outlet in data communication with the phone, and wherein the phone case is configured to transmit data to the phone through the communication element when at least one of the trigger is released, the needle is deployed, a safety catch is released, or contents of the reservoir are delivered.

* * * * *